US011219366B2

(12) United States Patent
Kook et al.

(10) Patent No.: US 11,219,366 B2
(45) Date of Patent: Jan. 11, 2022

(54) RETINA PHOTOGRAPHING APPARATUS AND RETINA PHOTOGRAPHING METHOD USING SAME

(71) Applicant: ROOTEEHEALTH, INC., Seongnam-si (KR)

(72) Inventors: Kyung Min Kook, Gyeonggi-do (KR); Su Ryeon Kim, Gyeonggi-do (KR)

(73) Assignee: ROOTEEHEALTH, INC., Gyeonggi-Do (KR)

( * ) Notice: Subject to any disclaimer, the term of this patent is extended or adjusted under 35 U.S.C. 154(b) by 238 days.

(21) Appl. No.: 16/482,956

(22) PCT Filed: Jan. 30, 2018

(86) PCT No.: PCT/KR2018/001296
§ 371 (c)(1),
(2) Date: Aug. 1, 2019

(87) PCT Pub. No.: WO2018/143651
PCT Pub. Date: Aug. 9, 2018

(65) Prior Publication Data
US 2019/0365224 A1 Dec. 5, 2019

(30) Foreign Application Priority Data

Feb. 1, 2017 (KR) .................. 10-2017-0014383
Jan. 30, 2018 (KR) .................. 10-2018-0011407

(51) Int. Cl.
*A61B 3/14* (2006.01)
*A61B 3/12* (2006.01)
*A61B 3/00* (2006.01)

(52) U.S. Cl.
CPC .............. *A61B 3/14* (2013.01); *A61B 3/12* (2013.01); *A61B 3/0041* (2013.01)

(58) Field of Classification Search
CPC ............ A61B 3/14; A61B 3/12; A61B 3/0041
(Continued)

(56) References Cited

U.S. PATENT DOCUMENTS

| 7,530,692 B2 * | 5/2009 | Yamaguchi | .......... A61B 3/1015 351/206 |
| 2006/0074461 A1 * | 4/2006 | Tano | .................. A61N 1/36046 607/54 |

(Continued)

FOREIGN PATENT DOCUMENTS

| JP | H11-225968 | 8/1999 |
| JP | 2000-041948 A | 2/2000 |

(Continued)

OTHER PUBLICATIONS

International Search Report and Written Opinion for PCT/KR2018/001296, dated May 14, 2018, 12 pages.

*Primary Examiner* — Mohammed A Hasan
(74) *Attorney, Agent, or Firm* — Burris Law, PLLC

(57) ABSTRACT

According to an embodiment of the present disclosure, there is provided a retina photographing apparatus including: a body unit including a case providing an outer appearance of the retina photographing apparatus, and a holder connected to the case and being mountable on an examinee's head; a retina photographing unit installed inside the case, and configured to irradiate light onto a retina of the examinee's left or right eye and to detect the light reflected from the retina to acquire an image of the retina; and a driving unit configured to move a position of the retina photographing unit inside the case in order to photograph both of the examinee's eyes.

11 Claims, 10 Drawing Sheets

(58) Field of Classification Search
USPC .......................................................... 351/206
See application file for complete search history.

(56) References Cited

U.S. PATENT DOCUMENTS

| | | | | |
|---|---|---|---|---|
| 2009/0153796 A1* | 6/2009 | Rabner | .................. | A61B 3/028 |
| | | | | 351/201 |
| 2013/0050644 A1* | 2/2013 | Van Saarloos | ........... | A61B 3/14 |
| | | | | 351/206 |

FOREIGN PATENT DOCUMENTS

| | | | |
|---|---|---|---|
| JP | 2002-318366 | A | 10/2002 |
| JP | 2003076353 | A | 3/2003 |
| JP | 2010-131166 | | 6/2010 |
| JP | 2016-105945 | | 6/2016 |
| JP | 2016-105945 | A | 6/2016 |
| JP | 2016-150017 | | 8/2016 |
| JP | 2016-221075 | A | 12/2016 |
| KR | 10-2010-0066391 | A | 6/2010 |
| WO | 2016179185 | | 11/2016 |
| WO | 2016194772 | A1 | 12/2016 |

* cited by examiner

RETINA PHOTOGRAPHING APPARATUS AND RETINA PHOTOGRAPHING METHOD USING SAME

RELATED APPLICATIONS

The present application is a U.S. national stage application under 35 U.S.C. § 371 of PCT Application No. PCT/KR2018/001296 filed Jan. 30, 2018, which claims priority to Korean Application Nos. 10-2017-0014383 filed Feb. 1, 2017, and 10-2018-0011407 filed Jan. 30, 2018, all of which are hereby incorporated in their entirety by reference as set forth herein.

TECHNICAL FIELD

Embodiments of the present disclosure relates to a retina photographing apparatus and a retina photographing method using the same.

BACKGROUND ART

The fundus is the rear part of the retina in the eyeball. Through a fundus examination, the centrocecal area, optic disc, retinal blood vessels, etc. located in the center of the retina are observed, and through a fundus examination, the relative seriousness of illnesses of hypertensive patients is determined, and also a diabetic ocular complication examination is performed. The shape of the optic disc is used to diagnose various optic nerve diseases, such as glaucoma, increased brain pressure, optic neuritis, ischemic neuropathy, etc., and also is essentially used to diagnose retinal diseases, such as macular degeneration, retinopathy of prematurity, etc. Particularly, through a fundus examination, an early diagnosis of glaucoma and macular degeneration which are two of the three major causes of loss of sight is possible.

Meanwhile, a typical fundus camera examines an examinee's fundus in a state of being fixed at a predetermined location. Therefore, an examinee needs to visit a medical institution such as hospital to have a fundus examination. However, examinees living in regions lacking medical institutions have difficulties in having fundus examinations.

DESCRIPTION OF EMBODIMENTS

Technical Problem

To overcome the above-described problem and/or limitation, there are provided a retina photographing apparatus capable of repeatedly acquiring an examinee's optimal images and a retina photographing method using the retina photographing apparatus.

Solution to Problem

According to an embodiment of the present disclosure, there is provided a retina photographing apparatus including: a body unit comprising a case providing an outer appearance of the retina photographing apparatus, and a holder connected to the case and being mountable on an examinee's head; a retina photographing unit installed inside the case, and configured to irradiate light onto a retina of the examinee's left or right eye and to detect the light reflected from the retina to acquire an image of the retina; and a driving unit configured to move a position of the retina photographing unit inside the case in order to photograph both of the examinee's eyes.

Advantageous Effects of Disclosure

The retina photographing apparatus according to embodiments of the present disclosure may be carried by a user to photograph the retina anywhere by stably fixing the body unit by using the holder the holder, and may acquire an accurate and clear image of the retina. Also, the retina photographing apparatus may include a driving unit capable of moving the location of a retina photographing unit inside the body unit to photograph both of an examinee's eyes under the same environmental condition upon being mounted once, thereby obtaining an accurate examination result.

BEST MODE

Figure 1:
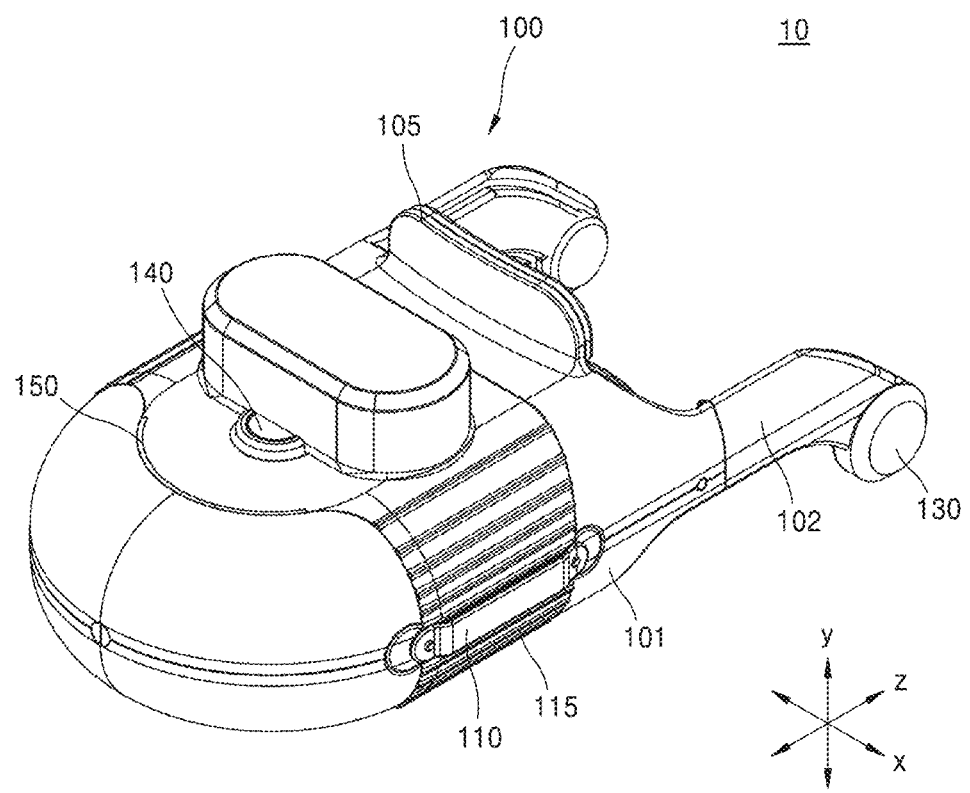
FIG. 1 is a perspective view showing a retina photographing apparatus according to an embodiment of the present disclosure.

According to an embodiment of the present disclosure, there is provided a retina photographing apparatus including: a body unit including a case forming an outer appearance of the retina photographing apparatus, and a holder connected to the case and being mountable on an examinee's head; a retina photographing unit installed inside the case, and configured to irradiate light onto a retina of the examinee's left or right eye and to detect the light reflected from the retina to acquire an image of the retina; and a driving unit configured to move a position of the retina photographing unit inside the case in order to photograph the examinee's both eyes.

According to an embodiment of the present disclosure, the retina photographing unit may include: a first light source configured to irradiate first light onto the retina of the examinee's left or right eye; a detector configured to detect the first light reflected from the retina; and an optical device including one or more lenses and a beam splitter, and configured to guide the first light irradiated from the first light source to the retina and to guide the first light reflected from the retina to the detector.

According to an embodiment of the present disclosure, the retina photographing unit may further include a second light source configured to irradiate second light onto the examinee's retina, the second light having a wavelength band that is different from a wavelength band of the first light, wherein the detector is configured to detect the first light and the second light reflected from the retina.

According to an embodiment of the present disclosure, the retina photographing apparatus may further include: a communication unit configured to receive an audio signal provided from the outside; and a speaker unit configured to transfer the received audio signal to the examinee.

According to an embodiment of the present disclosure, the speaker unit may be positioned at one side of the holder of the body unit.

According to an embodiment of the present disclosure, the retina photographing apparatus may further include a display unit positioned inside the case and providing a predetermined pattern image to the examinee's left or right eye.

According to an embodiment of the present disclosure, the display unit may provide a pattern image including a fixation point to the examinee's left or right eye.

According to another embodiment of the present disclosure, there is provided a retina photographing apparatus including: a body unit including a case forming an outer appearance; a retina photographing unit positioned inside the case, and configured to irradiate light onto a retina of an examinee's left or right eye and to detect the light reflected from the retina to acquire an image of the retina; a driving unit configured to move a position of the retina photographing unit inside the case in order to photograph the examinee's both eyes; and a control unit configured to receive first measurement position information for the examinee's left eye and second measurement position information for the examinee's right eye, acquired upon previous retina photographing, and to control, when the examinee wears the body unit, the driving unit to move the retina photographing unit to the first measurement position of the left eye or to the second measurement position of the right eye by using the first measurement position information or the second measurement position information.

According to an embodiment of the present disclosure, the first measurement position information may include first center-of-pupil coordinates for the left eye, the second measurement position information may include second center-of-pupil coordinates for the right eye, and the first center-of-pupil coordinates and the second center-of-pupil coordinates may be plane coordinates data with respect to a first axis and a second axis that is perpendicular to the first axis.

According to an embodiment of the present disclosure, the first measurement position information may further include first coordinates data and first focus position data with respect to a third axis that is perpendicular to the first axis and the second axis, and the second measurement position information may further include second coordinates data and second focus position data with respect to the third axis.

According to an embodiment of the present disclosure, the control unit may control the driving unit to move the retina photographing unit to the first center-of-pupil coordinates, and then re-adjust a position of the retina photographing unit using the first coordinates data and the first focus position data, or the control unit may control the driving unit to move the retina photographing unit to the second center-of-pupil coordinates and then re-adjust a position of the retina photographing unit using the second coordinates data and the second focus position data.

According to an embodiment of the present disclosure, the control unit may further receive distance data about a distance between the examinee's left eye and the examinee's right eye, and control the driving unit to move, after the retina photographing unit measures one of the left eye and the right eye, the retina photographing unit to the other one of the left eye and the right eye based on the distance data.

According to an embodiment of the present disclosure, the first measurement position information and the second measurement position information may be position information of the retina photographing unit in an optimal focusing condition upon previous retina photographing for the examinee.

According to an embodiment of the present disclosure, there is provided a retina photographing method using a portable retina photographing apparatus, including: moving, by a driving unit, a retina photographing unit to a position corresponding to an examinee's left or right eye inside a body unit; providing, by a display unit, a predetermined pattern image to the examinee's left or right eye; irradiating, by a retina photographing unit, light onto a retina of the examinee's left or right eye and detecting the light reflected from the retina to obtain a temporary image of the retina; adjusting, by a control unit, a position of the retina photographing unit based on the temporary image and the predetermined pattern image; and acquiring, by the retina photographing unit, an image of the retina.

According to an embodiment of the present disclosure, the adjusting of the position of the retina photographing unit may include: determine whether fovea and optic disc of the examinee's left or right eye exist in the temporary image; and adjusting, when neither the fovea nor the optic disc exist in the temporary image, the position of the retina photographing unit such that both the fovea and the optic disc exist in the temporary image and then aligning a center of the predetermined pattern image with a center of the fovea.

According to an embodiment of the present disclosure, the providing of the predetermined pattern image may include providing a pattern image including a fixation point to the examinee's left or right eye.

According to an embodiment of the present disclosure, the providing of the predetermined pattern image may include providing a pattern image that is used in a color-blindness test or a color-weakness test to the examinee's left or right eye.

MODE OF DISCLOSURE

Hereinafter, embodiments will be described in detail with reference to the accompanying drawings. In the following descriptions given with reference to the drawings, the same or corresponding components will be assigned like reference numerals, and overlapping descriptions thereof will be omitted.

The present embodiments may be modified variously, and therefore, specific embodiments are illustrated in the drawings and described in detail in the detailed description. Effects and features of the present embodiments and a method for achieving the effects and features will be apparent from the following contents given in detail with reference to the drawings. However, the present embodiments are not limited to the following embodiments, and may be implemented in various forms.

In the following embodiments, although the terms "first", "second", etc. may be used herein to describe various components, these components should not be limited by these terms. These terms are only used to distinguish one component from another.

In the following embodiments, it is to be understood that the singular forms "a," "an," and "the" include plural referents unless the context clearly dictates otherwise.

It will be understood that when the terms "includes," "comprises," "including," and/or "comprising," when used in this specification, specify the presence of stated features or components, but do not preclude the presence or addition of one or more other features or components.

It will also be understood that when a portion, such as a unit, a region, a component, etc., is referred to as being "on" another portion, it can be directly on the other portion, or an intervening unit, an intervening region or an intervening component may also be present.

Also, in the following embodiments, it will be understood that the case in which a certain portion is "connected" or "coupled" to another portion includes the case in which an intervening member between the two members exists, as well as the case in which the member is "directly and/or fixedly connected or coupled" to the other member, unless the context clearly dictates otherwise.

It will be understood that features or components written in the specification mean that they exist, but do not preclude the presence or addition of one or more other features or components.

For clarity and convenience of description, the sizes of the components may be more or less exaggeratedly shown in the drawings. For example, the size and thickness of each component shown in the drawings are arbitrarily shown for convenience of description, and the following embodiments are not limited to those shown in the drawings.

Figure 2:
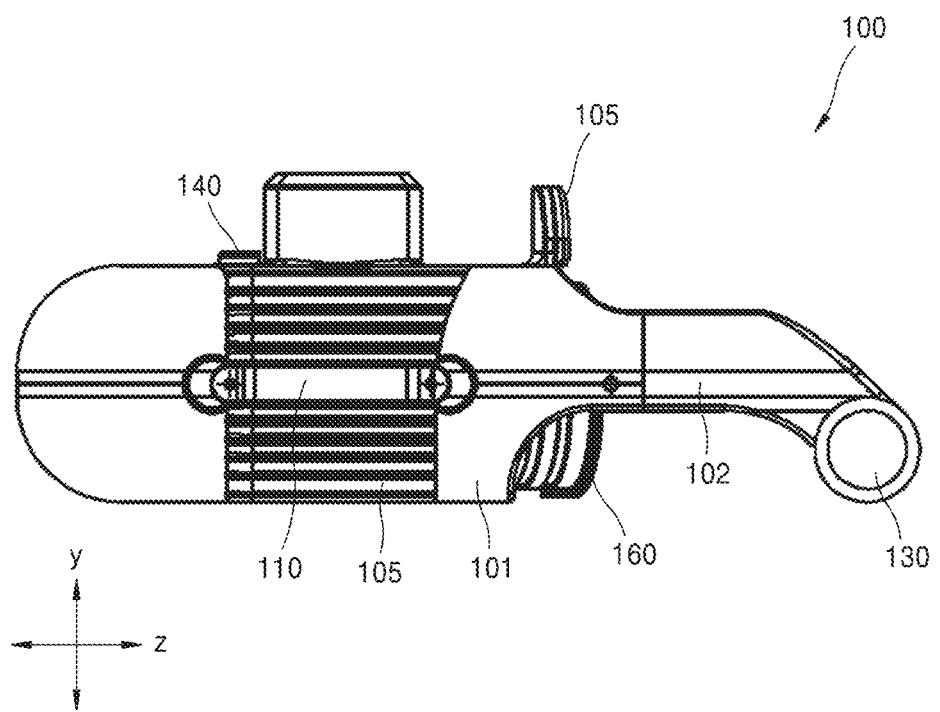
FIG. 2 is a side view of the retina photographing apparatus of FIG. 1.
Figure 3:
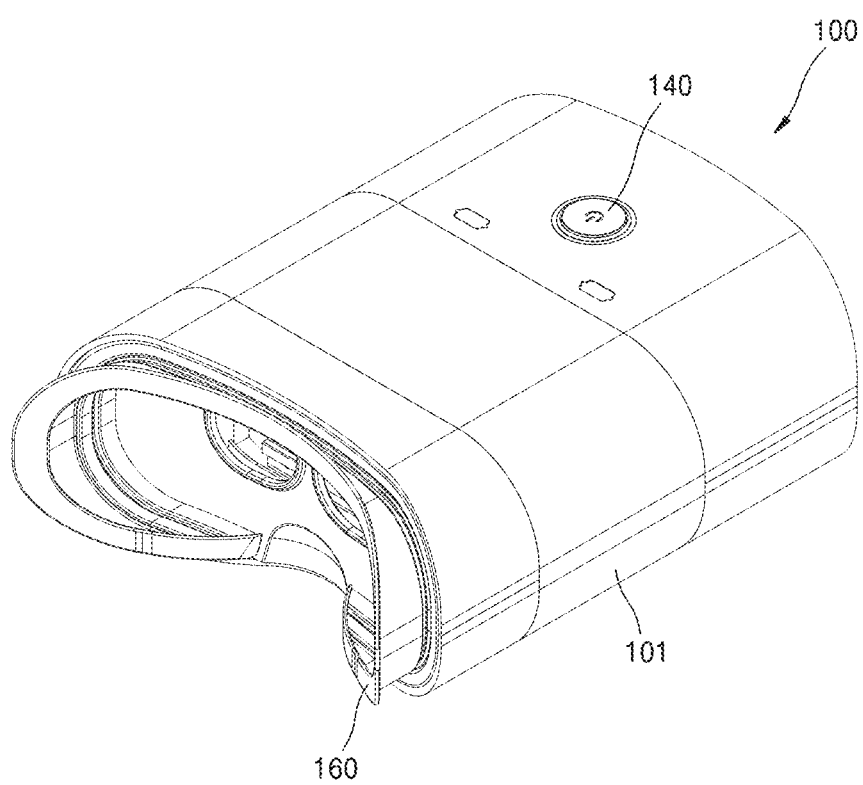
FIG. 3 shows another embodiment of the retina photographing apparatus of FIG. 1.
Figure 4:
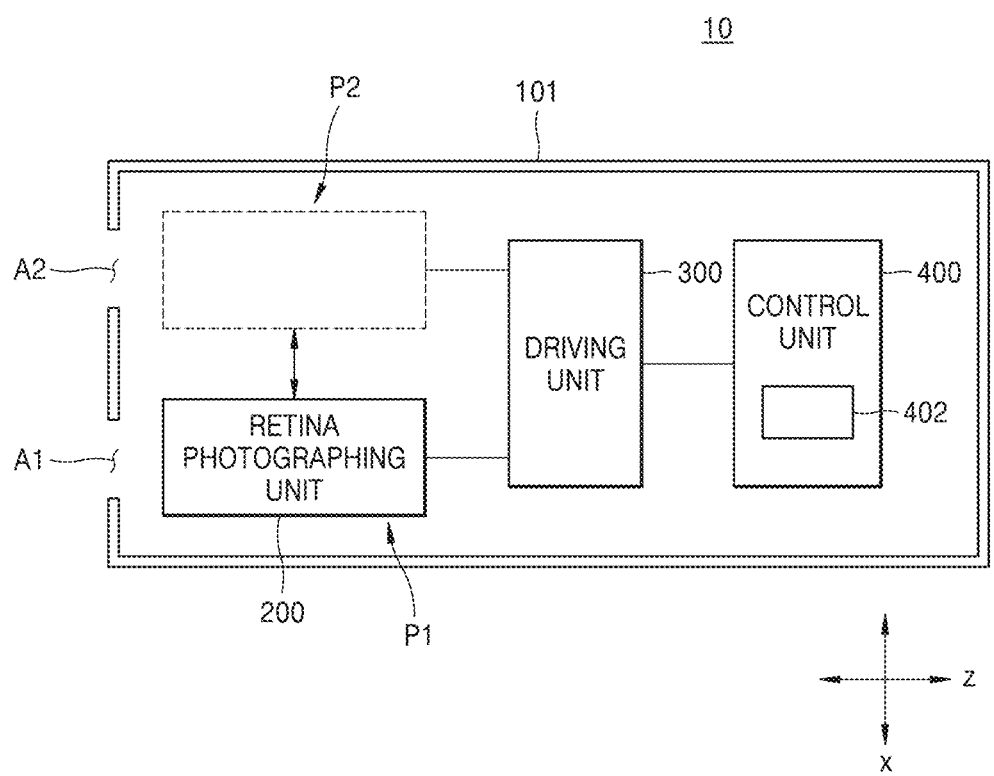
FIG. 4 is a block diagram schematically showing the retina photographing apparatus of FIG. 1.

FIG. 1 is a perspective view showing a retina photographing apparatus 10 according to an embodiment of the present disclosure, and FIG. 2 is a side view of the retina photographing apparatus 10 of FIG. 1. FIG. 3 shows another embodiment of the retina photographing apparatus 10 of FIG. 1, and FIG. 4 is a block diagram schematically showing the retina photographing apparatus 10 of FIG. 1.

Referring to FIGS. 1 to 4, the retina photographing apparatus 10 according to an embodiment of the present disclosure may include a body unit 100, a retina photographing unit 200, a driving unit 300, and a control unit 400.

The body unit 100 may include a case 101 and a holder 102. The case 101 may form an outer appearance of the retina photographing apparatus 10, and in the inside of the case 10, a cavity may be formed to accommodate the retina photographing unit 200 and the driving unit 300. In the case 101, a first opening A1 and a second opening A2 may be formed to correspond to an examinee's both eyes in order to enable the retina photographing unit 200 to photograph all retinas of the examinee's left and right eyes. Although not shown in the drawings, for convenience of description, cover glass for protecting the retina photographing unit 200 installed inside the case 101 or optical lenses for focusing light provided from the retina photographing unit 200 may be installed at the first opening A1 and the second opening A2.

According to another embodiment, as shown in FIG. 3, the body unit 100 may be configured only with the case 101 without the holder 102. When the body unit 100 is configured only with the case 101, an examinee may photograph the retina while holding the case 101 with his/her hand. However, the body unit 100 may include a separate holder to photograph the retina in a fixed state.

The holder 102 may be connected to the case 101, and may be formed in various shapes that can be mounted on an examinee's head. According to an embodiment, as shown in FIGS. 1 and 2, the holder 102 may be in the shape of eyeglass temples that are hanged on an examinee's both ears to support the body unit 100. However, the present disclosure is not limited to this, and the holder 102 may be in any other shape as long as it enables the retina photographing apparatus 10 including the body unit 100 to be stably mounted on an examinee's head. For example, the holder 102 may be in the form of an elastic band, helmets, or straps. According to another embodiment, the holder 102 may further include a forehead supporter 105 that contacts an examinee's forehead to support the body unit 100. The holder 102 according to the other embodiment may stably support the retina photographing apparatus 10 through the forehead supporter 105 when the retina is photographed.

According to another embodiment, the body unit 100 may further include a shading portion 160 positioned at an area of the case 101 toward an examinee's face and configured to prevent outside light from entering the examinee's both eyes. The shading portion 160 may be, when the examinee wears the retina photographing apparatus 100, a portion that the examinee's face contacts. The shading portion 160 may have a structure corresponding to the examinee's face curve. Also, the shading portion 160 may be stably in close contact with the examinee's face, and include an elastic material to effectively prevent outside light from entering the examinee's both eyes. In an area of the shading portion 160, a groove in which the examinee's nose is inserted may be formed. The shading portion 160 may provide a darkroom to the examinee's both eyes when the retina is photographed, thereby minimizing pupilary reflex. Thereby, the retina photographing apparatus 10 according to an embodiment of the present disclosure may acquire an accurate image for the examinee's retina.

Meanwhile, the body unit 100 may further include a handle 110 at one side of the case 101 to enable the examinee to easily and stably hold the case 101 when photographing the retina. Also, the body unit 100 may further include an uneven portion 115 on a surface of the case 101 that is adjacent to the handle 110, to prevent slipping. Also, the body unit 100 may further include a switch 140 for providing a power on/off signal to the retina photographing apparatus 10 according to an operation from the outside, and a display 150 displaying an operation state of the retina photographing apparatus 10, such as whether power of the retina photographing apparatus 10 is on, whether the retina photographing apparatus 10 has broken down, etc. The display 150 may include a light source displaying different colors according to operation states. For example, the display 150 may include a LED light source.

Meanwhile, the retina photographing unit 200 may be installed inside the case 101. The retina photographing unit 200 may irradiate light onto the retina of the examinee's left or right eye, and detect the light reflected from the retina to acquire an image of the retina.

The driving unit 300 may move a position of the retina photographing unit 200 inside the case 101 to measure the examinee's both eyes. The driving unit 300 may be connected to the retina photographing unit 200. The driving unit 300 may locate the retina photographing unit 200 at a position corresponding to any one of the examinee's left and right eyes, and then move the position of the retina photographing unit 200 to photograph the other one (P1⇋P2). For example, the driving unit 300 may include a linear actuator and a driving motor. However, the present disclosure is not limited to this, and the driving unit 300 may be any other power transfer apparatus that can provide power to the retina photographing unit 200.

The control unit 400 may receive first measurement position information about the examinee's left eye and second measurement position information about the examinee's right eye, obtained upon previous retina photographing. More specifically, the first measurement position information and the second measurement position information may be position information of the retina photographing unit 200 when images are acquired in an optimal focusing condition upon the previous retina photographing, and the first measurement position information and the second measurement position information may be stored in an external server. In other words, the retina photographing apparatus 10 may transmit the first measurement position information and the second measurement position information to the external server through a communication unit (not shown), and the first measurement position information and the second measurement position information may construct database in correspondence to examinee identification information. An examinee or user may use a user terminal capable of executing an application to request the server to provide the first measurement position information and the second measurement position information to the retina photographing apparatus 10. However, the present disclosure is not limited to this, and as another embodiment, the control unit 400 may include a memory 402 in which the first measurement position information and the second measurement position information have been stored in advance, instead of receiving the first measurement position information and the second measurement position information from the external server.

When the examinee wears the body unit 100, the control unit 400 may control the driving unit 300 to move the retina photographing unit 200 to the first measurement position of the left eye or to the second measurement position of the right eye, based on the first measurement position information and the second measurement position information.

The retina photographing apparatus 10 may store position information about a position at which the examinee has acquired an optimal image when he/she has previously photographed the retina using the retina photographing apparatus 10, and when the examinee photographs the retina next time, the retina photographing apparatus 10 may move the retina photographing unit 200 immediately to the position at which the optimal image has been acquired, by using the stored position information. Accordingly, the retina photographing apparatus 10 may need not to adjust the position of the retina photographing unit 200 whenever an examination is performed, thereby increasing convenience of an examinee's examination and acquiring accurate retina images.

More specifically, the first measurement position information and the second measurement position information may be an examinee's optimal position information acquired upon previous retina photographing for the examinee. The first measurement position information may include first center-of-pupil coordinates (x1, y1) for the left eye, and the second measurement position information may include second center-of-pupil coordinates (x2, y2) for the right eye. Herein, the first center-of-pupil coordinates (x1, y1) and the second center-of-pupil coordinates (x2, y2) may be plane coordinates data (x-y) with respect to a first axis (x axis) and a second axis (y axis) that is perpendicular to the first axis (x axis).

Also, the first measurement position information may include first coordinates data z1 and first focus position data f1 with respect to a third axis (z axis) that is perpendicular to the first axis (x axis) and the second axis (y axis). Likewise, the second measurement position information may include second coordinates data z2 and second focus position data f2 with respect to the third axis (z axis). In other words, the first measurement position information and the second measurement position information may be 4-axis coordinates data with respect to four axes of x-y-z-f.

According to an embodiment, the control unit 400 may move the retina photographing unit 200 to the first center-of-pupil coordinates (x1, y1), and then re-adjust the position of the retina photographing unit 200 using the first coordinates data z1 and the first focal position data f1, or the control unit 400 may move the retina photographing unit 200 to the second center-of-pupil coordinates (x2, y2) and then re-adjust the position of the retina photographing unit 200 using the second coordinates data z2 and the second focal position data f2. According to another embodiment, the control unit 400 may move the retina photographing unit 200 immediately using the 4-axis coordinates data of the first measurement position information and the second measurement position information. However, because detecting the position of the pupil is more or less easier than detecting the position of the retina, the control unit 400 may control the retina photographing unit 200 to move to the center-of-pupil coordinates on the x-y plane and to then move along the z axis, and perform focusing, thereby improving adjustment easiness and position accuracy of the retina photographing unit 200.

Meanwhile, the control unit 400 may further store distance data about a distance between the examinee's left eye and the examinee's right eye in the memory 402. The control unit 400 may control, after the retina photographing unit 200 measures any one of the left eye and the right eye, the driving unit 300 to move the retina photographing unit 200 to the other eye based on the distance data.

Meanwhile, the retina photographing apparatus 10 may further include, although not shown, a communication unit (not shown) for receiving audio signals provided from the outside and a speaker unit 130 for transferring the received audio signal to the examinee. The communication unit (not shown) may receive audio signals from the outside through wired communication or wireless communication, such as Bluetooth, wireless LAN, near field communication (NFC), or the like. The speaker unit 130 may be positioned at one side of the holder 102 of the body unit 100 to be adjacent to the examinee's ear. The speaker unit 130 may be a bone conduction speaker for outputting received audio signals through bone conduction, according to an embodiment. However, the present disclosure is not limited to this, and the speaker unit 130 may be a speaker capable of outputting received audio signals to the examinee through the air.

Also, the retina photographing apparatus 10 may further include an input unit (not shown) for generating, when an examinee wears the body unit 100, an input signal indicating that an examinee wears the body unit 100. The input unit (not shown) may include an inputter (not shown), such as a switch or button, for enabling an examinee to manually inform wearing of the body unit 100 or an examination start. When an examinee presses a button, the input unit (not shown) may generate an input signal and provide it to the control unit 400. According to another embodiment, the input unit (not shown) may include a sensor (not shown) for generating an input signal when an examinee wears the body unit 100. The sensor (not shown) may sense an examinee's wearing operation or an examinee's body part to generate an input signal. The sensor (not shown) may further include a GPS sensor or a gyro sensor to acquire position information of the retina photographing apparatus 10 provided from the aforementioned sensors. In this case, the control unit 400 may determine whether the examinee is properly wearing the retina photographing apparatus 10, based on the position information and the input signal, and when the control unit 400 determines that the examinee is properly wearing the retina photographing apparatus 10, the control unit 400 may start photographing the retina.

Hereinafter, the retina photographing unit 200 according to an embodiment of the present disclosure will be described in detail.

Figure 5:
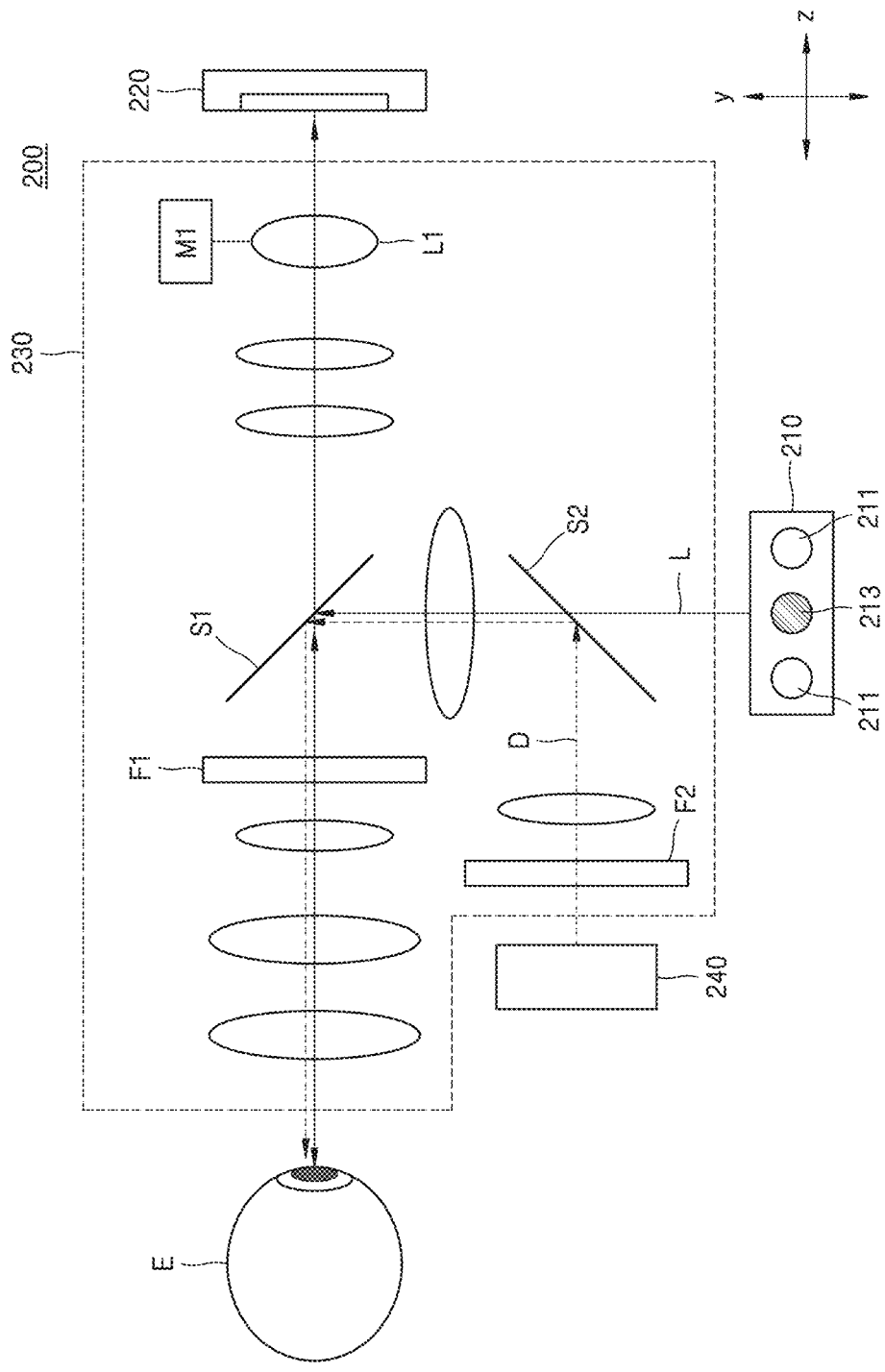
FIG. 5 schematically shows an optical structure of the retina photographing apparatus of FIG. 4.

FIG. 5 schematically shows an optical structure of the retina photographing apparatus 200 of FIG. 4.

Referring to FIGS. 4 and 5, the retina photographing unit 200 may include a first light source 211, a second light source 213, a detector 220, and an optical device 230.

The first light source 211 may irradiate first light onto a retina of an examinee's left or right eye, and the second light source 213 may irradiate second light onto the retina of the examinee's left or right eye. Herein, the second light may have a wavelength band that is different from that of the first light. The first light may be white light having a wavelength band of 450 nm to 650 nm, and the second light may be infrared light having a wavelength band of 750 nm to 950 nm. According to another embodiment, the second light source 213 may include a plurality of light sources capable of irradiating a plurality of wavelength bands, and the second light source 213 may combine two or more of the plurality of wavelength bands to irradiate the second light, as necessary. For example, to determine a glucose level, the second light source 213 may irradiate light of a wavelength band of 650 nm to 670 nm or light of a wavelength band of 800 nm to 1300 nm. Also, for autofluorescence photography, the second light source 213 may irradiate light of a wavelength band of 470 nm to 490 nm, a wavelength band of 790 nm to 810 nm, and a wavelength of 450 nm. At this time, the light of the wavelength band of 470 nm to 490 nm, the wavelength band of 790 nm to 810 nm, and the wavelength of 450 nm may be used for autofluorescence photography of lipofuscin, melanin, and flavoprotein. Also, to measure advanced glycation end products (AGEs), the second light source 213 may irradiate light of a wavelength band of 370 nm to 400 nm. Also, to measure hemoglobin or deoxyhemoglobin, the second light source 213 may irradiate light of a wavelength band of 570 nm to 580 nm, light of a wavelength of 750 nm, and light of a wavelength of 800 nm. The second light source 213 may irradiate light of different wavelength bands simultaneously or sequentially onto the retina of the examinee's left or right eye.

The retina photographing apparatus 10 according to an embodiment of the present disclosure may determine a position of a retina or an eyeball E by using the second light source 213 of irradiating infrared light, and photograph the retina by using the first light source 211 of irradiating white light. However, the present disclosure is not limited to this, and the retina photographing apparatus 10 may photograph the retina by using the second light source 213.

The detector 220 may detect the first light and/or second light reflected from the retina. The detector 220 may include sensing means capable of sensing the first light and the second light. For example, the detector 220 may be a complementary metal-oxide semiconductor (CMOS) image sensor that photographs images when a light source of a visible light wavelength band and/or a light source of an infrared light wavelength band is used.

The optical device 230 may include light path changing means 51, such as one or more lenses and prisms or a beam splitter, and guide the first light irradiated from the first light source 211 to the retina and the first light reflected from the retina to the detector 220. At this time, the optical device 230 may guide the second light irradiated from the second light source 213, as well as the first light irradiated from the first light source 211, to the retina, and guide the second light reflected from the retina to the detector 220. Hereinafter, for convenience of description, the first light source 211 and the second light source 213 are defined as a light source 210, and the first light and the second light are defined as light L having the same light path.

The optical device 230 may change a path of light L irradiated from the light source 210 by using the light path changing means S1, irradiate the light L onto the retina of the examinee's eyeball E, and provide the light L reflected from the retina to the detector 220. The light source 230 may include at least one lens for focusing light L on the light path to provide the focused light L to the retina or the detector 220. Also, the optical device 230 may further include an autofocusing actuator M1 connected to the lens L1 positioned on a path of the light L provided to the detector 220 and configured to enable the lens L1 to perform autofocusing. In the drawing, the auto focusing actuator M1 is shown to be connected to one lens L1. However, the present disclosure is not limited to this. The auto focusing actuator M1 may be connected to a lens module including one or more lenses.

Meanwhile, the retina photographing apparatus 10 according to an embodiment may further include a display unit 240 installed inside the case 101 and providing a pattern image including a predetermined pattern to the examinee's left or right eye. The pattern image may be an image including a fixation point for fixing the examinee's eye when the retina is photographed. According to another embodiment, the pattern image may include a pattern that is used in an examinee's eyesight test, such as a color-blindness/color-weakness test.

At this time, the optical device 230 may further guide a pattern image D provided from the display unit 240 to the examinee's retina. The display unit 240 may be positioned at a location that is different from that of the light source 210 inside the case 101 of the body unit 100. The optical device 230 may further include second light path changing means S2 for changing a path of the pattern image D provided from the display unit 240 and guiding the pattern image D to the retina. Also, the optical device 230 may further include a first polarizing plate F1 and a second polarizing plate F2 for preventing cornea reflection and back-scattering. The first polarizing plate F1 may be positioned between the first light path changing means S1 and the eyeball E, and the second polarizing plate F2 may be positioned between the display unit 240 and the second light path changing means S2, wherein an optical axis of the first polarizing plate F1 may be perpendicular to an optical axis of the second polarizing plate F2.

Figure 6:
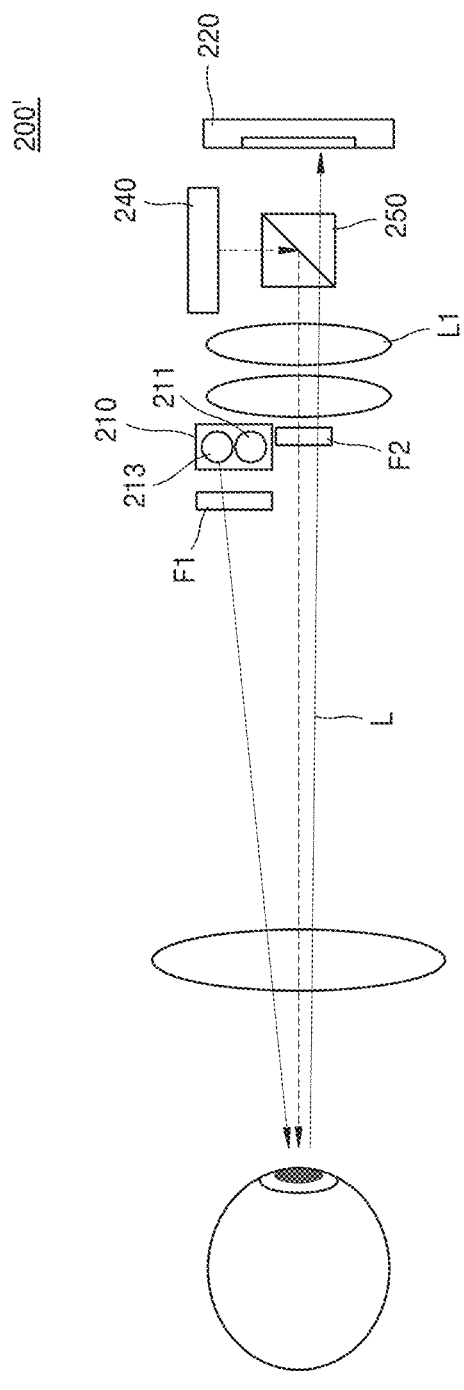
FIG. 6 schematically shows another embodiment of the optical structure of the retina photographing apparatus of FIG. 4.

FIG. 6 schematically shows another embodiment of the optical structure of the retina photographing apparatus 200 of FIG. 4.

Referring to FIGS. 4 and 6, the retina photographing unit 200 according to another embodiment may be different from the retina photographing unit 200 of FIG. 5 in that the display unit 240 is positioned adjacent to the detector 220 and the light source 210 including the first light source 211 and the second light source 213 irradiates light by an off-axis method. In the present specification, like reference numerals represent like components, and for convenience of description, overlapping descriptions will be omitted.

The first light source 211 may irradiate first light onto a retina of an examinee's left or right eye, and the second light source 213 may irradiate second light onto the retina of the examinee's left or right eye. The first light source 211 and the second light source 213 may irradiate light onto the examinee's left or right eye by the off-axis method, as shown in the drawings, thereby preventing the irradiated light from being reflected from the pupil, instead of the retina, and then entering the detector 220.

The detector 220 may detect the first light and/or the second light reflected from the retina. The detector 220 may include sensing means capable of sensing the first light and the second light. For example, the detector 220 may be a CMOS image sensor for capturing images when a light source of a visible light wavelength band and/or a light source of an infrared light wavelength band is used.

The optical device 230 may include light path changing means 250, such as one or more lenses and prisms or a beam splitter, and guide light irradiated from the first light source 211 and the second light source 213 to the retina and light reflected from the retina to the detector 220.

The optical device 230 may further guide a pattern image D provided from the display unit 240 to the examinee's retina by using the light path changing means 250. The display unit 240 may be positioned adjacent to the detector 220, unlike the retina photographing unit 200 of FIG. 5. The light path changing means 250 may change a path of the pattern image D provided from the display unit 240 to guide the pattern image D to the retina, while passing the light reflected from the retina to guide the reflected light to the detector 220.

Hereinafter, a retina photographing method using the retina photographing apparatus 10 according to an embodiment of the disclosure will be described in detail with reference to FIGS. 7 and 8.

Figure 7:
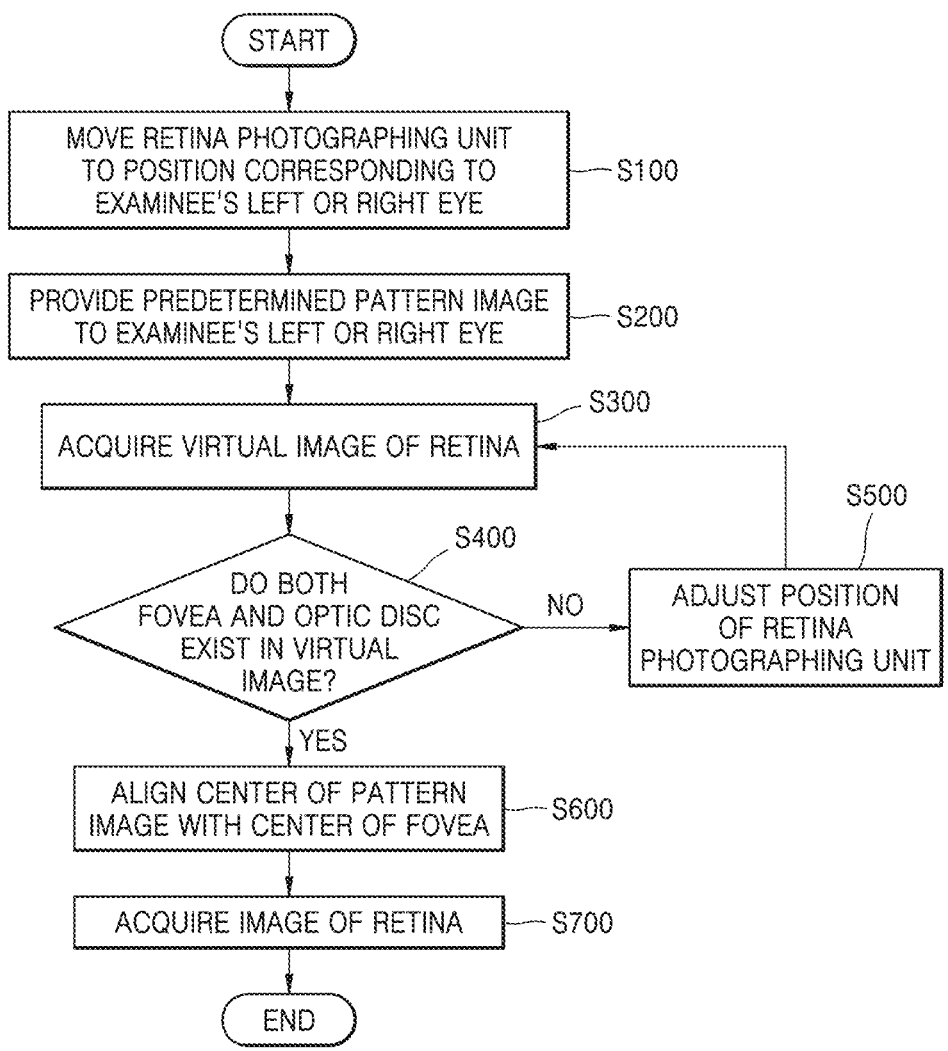
FIG. 7 is a flowchart sequentially showing a retina photographing method of a retina photographing apparatus, according to an embodiment of the present disclosure.
Figure 8:
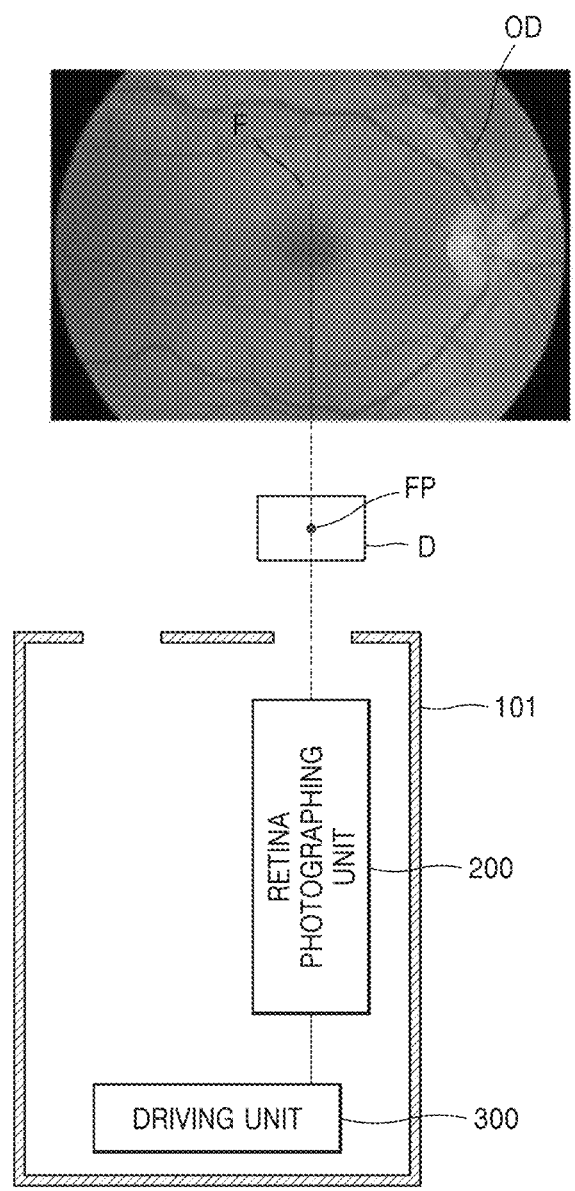
FIG. 8 is a conceptual view schematically showing a method of photographing a retina by using the retina photographing apparatus of FIG. 1.

FIG. 7 is a flowchart sequentially showing a retina photographing method of the retina photographing apparatus 10 according to an embodiment of the present disclosure, and FIG. 8 is a conceptual view schematically showing a method of photographing a retina by using the retina photographing apparatus 10 of FIG. 1.

Referring to FIGS. 7 and 8, when an examinee wears a retina photographing apparatus including body unit, a retina photographing unit, a driving unit, a display unit, and a control unit, the driving unit may move the retina photographing unit to a position corresponding to the examinee's left or right eye inside the body unit, in operation S100. As described above, the driving unit may be connected to the retina photographing unit, and move the retina photographing unit inside the body unit to photograph a retina of the examinee's one eye and then photograph a retina of the examinee's other eye.

Thereafter, the display unit may provide a predetermined pattern image D to the examinee's left or right eye, in other words, the examinee's one eye which the retina photographing unit moves to photograph, in operation S200. The predetermined pattern image D may include a fixation point FP for fixing the examinee's eye.

Then, the retina photographing unit including a light source, an optical device, and a detector may irradiate light onto the retina of the examinee's left or right eye, and detect the light reflected from the retina to acquire a temporary image of the retina, in operation S300. The temporary image of the retina may be acquired in real time and may be used to align a position of the retina photographing unit.

Thereafter, the control unit may adjust a position of the retina photographing unit based on the temporary image and the pattern image D. More specifically, the control unit may determine whether both fovea F and optic disc OD of the examinee's left or right eye exist in the temporary image, in operation S400. When both the fovea F and the optic disc OD of the examinee's left or right eye exist in the temporary image, the control unit may align the center of the pattern image D with the center of the fovea F, in operation S600. The pattern image D may be an image including a fixation point FP, and the control unit may control the driving unit to align the fixation point FP located at the center of the pattern image D with the center of the fovea F, thereby finely adjusting the position of the retina photographing unit 200.

When neither the fovea F nor the optic disc OD exist in the temporary image or when one of the fovea F and the optic disc OD exist in the temporary image, the control unit may control the driving unit to adjust the position of the retina photographing unit, in operation S500. The control unit may broadly adjust the position of the retina photographing unit until both the fovea F and the optic disc OD exist in the temporary image, and then finely adjust the position of the retina photographing unit to align the center of the fixation point FP with the center of the fovea F. As such, by using the retina photographing unit aligned to the retina of the examinee's left or right eye, an accurate and clear image of the retina may be acquired, in operation S700.

Figure 9:
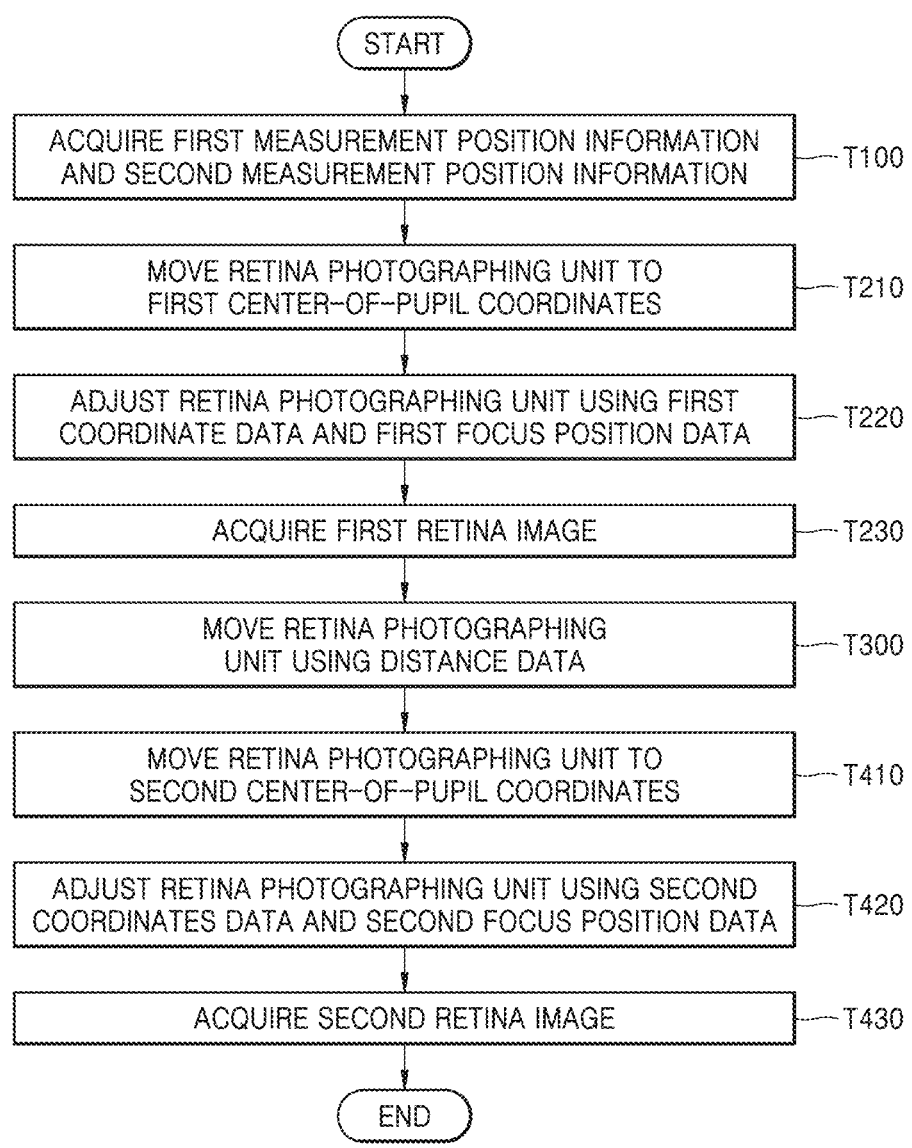
FIG. 9 is a flowchart sequentially showing a retina photographing method using a retina photographing apparatus, according to another embodiment of the present disclosure.
Figure 10:
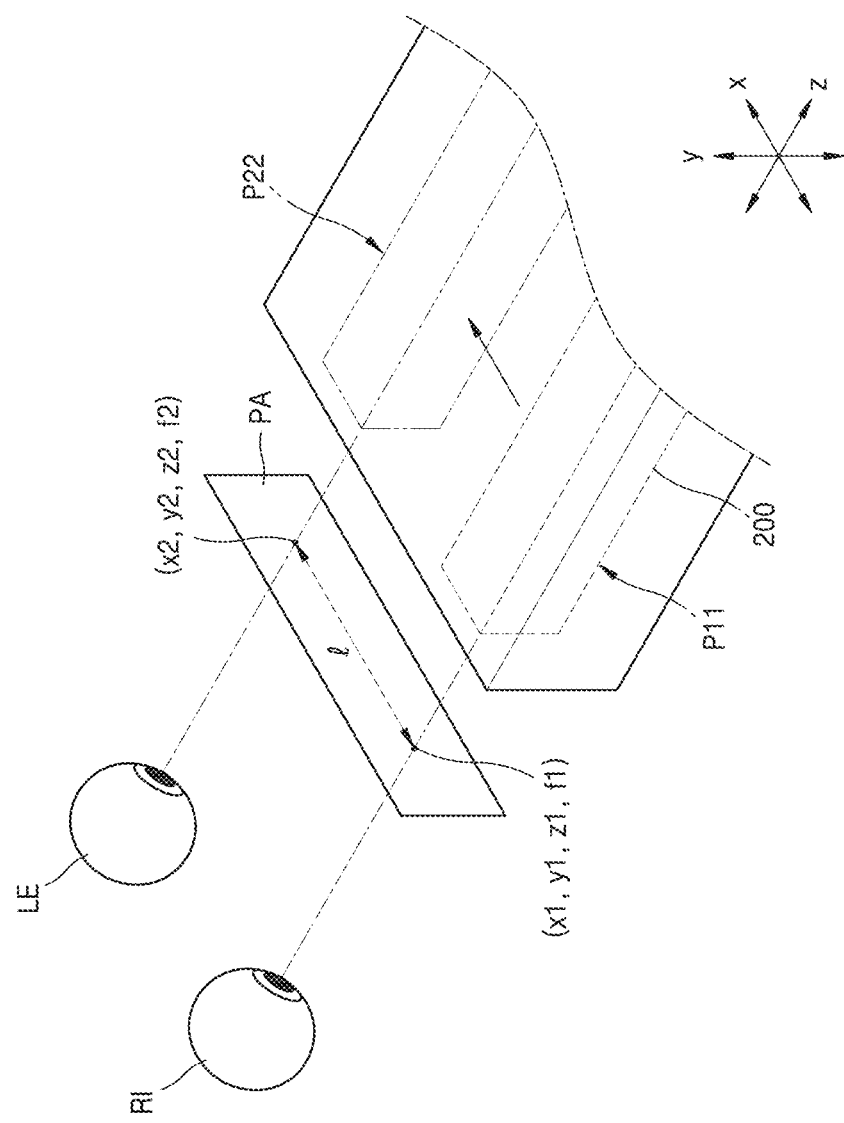
FIG. 10 is a conceptual view for describing the retina photographing method of FIG. 9.

FIG. 9 is a flowchart sequentially showing a retina photographing method using the retina photographing apparatus 10 according to another embodiment of the present disclosure, and FIG. 10 is a conceptual view for describing the retina photographing method of FIG. 9.

The retina photographing method using the retina photographing apparatus 10 as shown in FIGS. 7 and 8 is a retina photographing method when an examinee first photographs the retina using the retina photographing apparatus 10 or when position information of the retina needs to be updated. Accordingly, when optimal position information for acquiring an image of a retina has been stored by the above-described method, the retina photographing method which will be described below may be used to easily photograph the retina.

Referring to FIGS. 9 and 10, the control unit may receive first measurement position information and second measurement position information which are optimal position information deduced by the retina photographing method of FIG. 7, from an external server, in operation T100. The first measurement position information and the second measurement position information may be position information about a position of the retina photographing unit 200 in an optimal focusing condition upon previous retina photographing. The optimal focusing condition may be determined by an autofocusing algorithm. However, the present disclosure is not limited to this, and the optimal focusing condition may be selected manually by an external reader or an external examiner. The external reader or the external examiner may read a plurality of retina images for an examinee, and select an image with a most accurate focus from among the plurality of retina images. The optimal focusing condition may be position information of the retina photographing unit 200 when an image with a most accurate focus is photographed. However, hereinafter, for convenience of description, a case in which the optimal focusing condition is determined by an autofocusing algorithm will be described.

Herein, the autofocusing algorithm may use a contrast detection method or a phase difference detection method. The control unit may acquire an optimal retina image using the autofocusing algorithm, and store position information when the optimal retina image is acquired, in the memory.

Thereafter, when the examinee again wears the retina photographing apparatus 10 to photograph the retina, the control unit may move the retina photographing unit 200 to a first position P11 using any one of the first measurement position information and the second measurement position, and then photograph the retina to acquire a first retina image. In FIG. 10, a case in which a retina image for a right eye RI is acquired and then a retina image for a left eye LE is acquired is shown, however, a technical concept of the present disclosure is not limited thereto. Hereinafter, for convenience of description, a case in which a right eye RI is photographed and then a left eye LE is photographed will be described.

More specifically, the control unit may move the retina photographing unit 200 to the first center-of-pupil coordinates (x1, y1) included in the first measurement position information, in operation T210. The first center-of-pupil coordinates (x1, y1), which are coordinates data on a x-y plane PA, may be coordinates data on a plane PA that is perpendicular to an extension line connecting the center of the retina photographing unit 200 to the center of the retina. Then, the control unit may adjust a position of the retina photographing unit 200 using first coordinate data z1 and first focus position data f1, in operation T220. Then, the retina photographing unit 200 may photograph the retina of the right eye RI to acquire a first retina image, in operation T230.

The control unit may control the retina photographing unit 200 to move immediately to the first position P11 at which the retina photographing unit 200 has acquired an optimal image upon previous retina photographing, by using first measurement position information (x1, y1, z1, f1) which is four-axis coordinate data. However, because detecting the position of the pupil is more or less easier than detecting the position of the retina, the control unit may control the retina photographing unit 200 to move to the first center-of-pupil coordinates (x1, y1) on the x-y plane PA, then to move along the z-axis using the first coordinates data z1, and to perform focusing using the first focus position data f1. Thereby, the retina photographing apparatus 10 may improve adjustment easiness and position accuracy of the retina photographing unit 200.

Thereafter, the control unit may move the retina photographing unit 200 to the other eye, that is, the left eye L using distance data 1 stored in the memory, in operation T300. Herein, the distance data 1 may be a distance between the first center-of-pupil coordinates (x1, y1) and the second center-of-pupil coordinates (x2, y2). However, the distance data 1 may also be represented as a distance on the x axis to facilitate adjustment of the retina photographing unit 200. In other words, the distance data 1 may be represented as |x1-x2|.

Thereafter, the control unit may move the retina photographing unit 200 to a second position P22 by using the second measurement position information, and then photograph the retina to acquire a second retina image. More specifically, the control unit may move the retina photographing unit 200 to the second center-of-pupil coordinates (x2, y2) included in the second measurement position information, in operation T410. The second center-of-pupil coordinates (x2, y2) which are coordinates data on the x-y plane PA may be coordinates data on the plane PA that is perpendicular to an extension line connecting the center of the retina photographing unit 200 to the center of the retina. Then, the control unit may adjust a position of the retina photographing unit 200 using second coordinates data z2 and second focus position data f2, in operation T420. Then, the retina photographing unit 200 may photograph the retina of the left eye LE to acquire a second retina image, in operation T430.

Meanwhile, the retina photographing method using the retina photographing apparatus according to an embodiment may further include operation of comparing the first retina image or the second retina image with an image captured previously in the optimal focusing condition. Although the first measurement position information and the second measurement position information are position information of the retina photographing unit in the optimal focusing condition, the position of the retina photographing unit may change according to a change of the examinee's body, a change in wearing habit of the examinee wearing the retina photographing apparatus, etc. When a difference between the first retina image or the second retina image and the image previously captured in the optimal focusing condition is made due to the above-mentioned changes, the control unit may again photograph the retina by the retina photographing method of FIG. 5, and store first focus position information and second focus position information obtained by again photographing the retina in the memory, thereby correcting the first measurement position information and the second measurement position information.

As described above, the retina photographing apparatus according to an embodiment of the present disclosure may be carried by a user to photograph the retina anywhere by stably fixing the body unit with the holder, and may acquire an accurate and clear image of the retina. Also, the retina photographing apparatus may include the driving unit capable of moving the position of the retina photographing unit inside the body unit to photograph an examinee's both eyes under the same environmental condition when being once mounted, thereby deducing an accurate examination result. Also, the retina photographing method of the retina photographing apparatus according to an embodiment of the present disclosure may broadly move the retina photographing unit until both an examinee's fovea and optic disc exist in a temporary image when the temporary image is photographed, and then finely adjust the position of the retina photographing unit such that the retina photographing unit is located at the center of the fovea, thereby quickly and accurately aligning the retina photographing unit to the retina.

Also, the retina photographing apparatus according to an embodiment of the present disclosure may photograph a retina quickly and accurately upon re-measurement by omitting a more or less complicated alignment operation by using position information of the retina photographing unit acquired in a previous optimal focusing condition.

While the present disclosure has been particularly shown and described with reference to embodiments thereof, it will be understood by one of ordinary skill in the art that various changes in form and details may be made therein without departing from the scope of the disclosure as defined by the following claims. The embodiments should be considered in a descriptive sense only and not for purposes of limitation. Therefore, the scope of the disclosure is defined not by the detailed description of the disclosure but by the following claims, and all differences within the scope will be construed as being included in the present disclosure.

INDUSTRIAL APPLICABILITY

According to the present disclosure, a retina photographing apparatus is provided. Also, the embodiments of the present disclosure can be applied to cases of photographing the retina, fundus, eyeball, cornea, etc.

We claim:

1. A retina photographing apparatus comprising:
a body unit comprising a case providing an outer appearance of the retina photographing apparatus which is portable, and a holder connected to the case and being mountable on an examinee's head;
a retina photographing unit installed inside the case, and configured to irradiate light onto a retina of the examinee's left or right eye and detect the light reflected from the retina, the retina photographing unit operable to acquire an image of the retina;
a driving unit arranged to be inside the case and configured to move a position of the retina photographing unit inside the case such that the retina photographing unit photographs both of the examinee's eyes; and
a display unit positioned inside the case and providing a predetermined pattern image to the examinee's left or right eye, the pattern image including a fixation point to the examinee's left or right eye;
wherein the driving unit is further operable to locate the position of the retina photographing unit and adjust the position to an optimal position by using stored position information.

2. The retina photographing apparatus of claim 1, wherein the retina photographing unit further comprises:
a first light source configured to irradiate first light onto the retina of the examinee's left or right eye;
a detector configured to detect the first light reflected from the retina; and
an optical device comprising one or more lenses and a beam splitter, and configured to guide the first light irradiated from the first light source to the retina and to guide the first light reflected from the retina to the detector.

3. The retina photographing apparatus of claim 2, wherein the retina photographing unit further comprises a second light source configured to irradiate second light onto the examinee's retina, the second light having a wavelength band that is different from a wavelength band of the first light, wherein the detector is configured to detect the first light and the second light reflected from the retina.

4. The retina photographing apparatus of claim 1, further comprising:
a communication unit configured to receive an external audio signal; and
a speaker unit configured to transfer a received audio signal to the examinee.

5. The retina photographing apparatus of claim 4, wherein the speaker unit is positioned at one side of the holder of the body unit.

6. A retina photographing apparatus comprising:
a body unit comprising a case providing an outer appearance;
a retina photographing unit positioned inside the case, and configured to irradiate light onto a retina of an examinee's left or right eye and to detect the light reflected from the retina to acquire an image of the retina;
a driving unit configured to move a position of the retina photographing unit inside the case in order to photograph both of the examinee's eyes; and
a control unit configured to receive first measurement position information indicative of first optimal position for the examinee's left eye and second measurement position information indicative of second optimal position for the examinee's right eye, acquired upon previous retina photographing, and to control, while the examinee wears the body unit, the driving unit to move the retina photographing unit to the first measurement position of the left eye or to the second measurement position of the right eye by using the first measurement position information or the second measurement position information;
wherein the control unit further receives distance data about a distance between the examinee's left eye and the examinee's right eye, and controls the driving unit to move, after the retina photographing unit measures one of the left eye and the right eye, the retina photographing unit to the other one of the left eye and the right eye based on the distance data.

7. The retina photographing apparatus of claim 6, wherein the first measurement position information comprises first center-of-pupil coordinates for the left eye, the second measurement position information comprises second center-of-pupil coordinates for the right eye, and the first center-of-pupil coordinates and the second center-of-pupil coordinates are plane coordinates data with respect to a first axis and a second axis that is perpendicular to the first axis.

8. The retina photographing apparatus of claim 7, wherein the first measurement position information further comprises first coordinates data and first focus position data with respect to a third axis that is perpendicular to the first axis and the second axis, and the second measurement position information further comprises second coordinates data and second focus position data with respect to the third axis.

9. The retina photographing apparatus of claim 8, wherein the control unit controls the driving unit to move the retina photographing unit to the first center-of-pupil coordinates, and then re-adjusts a position of the retina photographing unit using the first coordinates data and the first focus position data, or the control unit controls the driving unit to move the retina photographing unit to the second center-of-pupil coordinates and then re-adjusts a position of the retina photographing unit using the second coordinates data and the second focus position data.

10. A retina photographing method using a portable retina photographing apparatus, comprising:
moving, by a driving unit, a retina photographing unit to a position corresponding to an examinee's left or right eye inside a body unit;
providing, by a display unit, a predetermined pattern image to the examinee's left or right eye;
irradiating, by a retina photographing unit, light onto a retina of the examinee's left or right eye and detecting the light reflected from the retina to obtain a temporary image of the retina;
adjusting, by a control unit, a position of the retina photographing unit based on the temporary image and the predetermined pattern image; and
acquiring, by the retina photographing unit, an image of the retina;
wherein providing of the predetermined pattern image further comprises:
providing the predetermined pattern image including a fixation point to the examinee's left or right eye; and providing the pattern image that is used in a color-blindness test or a color-weakness test to the examinee's left or right eye.

11. The retina photographing method of claim 10, wherein the adjusting of the position of the retina photographing unit comprises:

determine whether a fovea and an optic disc of the examinee's left or right eye exist in the temporary image; and adjusting, when neither the fovea nor the optic disc exist in the temporary image, the position of the retina photographing unit such that both the fovea and the optic disc exist in the temporary image and then aligning a center of the predetermined pattern image with a center of the fovea.

\* \* \* \* \*